United States Patent
Matur et al.

(10) Patent No.: US 7,402,414 B2
(45) Date of Patent: Jul. 22, 2008

(54) ENZYMATIC PROCESS FOR DEACETYLATION OF A PHENOXY-ALKYNYL ACETATE TO THE CORRESPONDING ALCOHOL

(75) Inventors: Ramesh V. Matur, Ridgewood, NJ (US); Mark E. Ruppen, Garnerville, NY (US)

(73) Assignee: Wyeth, Madison, NJ (US)

( * ) Notice: Subject to any disclaimer, the term of this patent is extended or adjusted under 35 U.S.C. 154(b) by 410 days.

(21) Appl. No.: 11/146,731

(22) Filed: Jun. 7, 2005

(65) Prior Publication Data

US 2005/0272725 A1    Dec. 8, 2005

Related U.S. Application Data

(60) Provisional application No. 60/577,791, filed on Jun. 8, 2004.

(51) Int. Cl.
*C12P 7/02* (2006.01)
*C12N 9/16* (2006.01)
*C12N 9/20* (2006.01)

(52) U.S. Cl. .................. 435/155; 435/198; 435/196

(58) Field of Classification Search .................. 435/155, 435/196, 198
See application file for complete search history.

(56) References Cited

OTHER PUBLICATIONS

Singh et al., Synthetic and novel biocatalytic resolution studies on (+/−)-5/6/7-acetoxy-4-aryl-3,4-dihydro-coumarins, Bioorganic & Medicinal Chemistry, vol. 11, 2003, pp. 529-538.
Kawaski et al., Lipase-catalyzed enantioselective deacetylation of ortho-substituted phenyl acetates with 1-butanol in organic solvents, Journal of Molecular Catalysis B: Enzymatic, vol. 6, 1999, pp. 447-451.
Poonam et al., Synthesis and lipase-mediated stereoselective deacetylation of (+/−)-3-acetoxymethyl-3-alkyl-7-methoxy-chroman-4-ones, Tetrahedron, vol. 57, 2001, pp. 7395-7402.
Iglesias et al., Complete and regioselective deacetylation of peracetylated uridines using a lipase, Biotechnology Letters, vol. 22, 2000, pp. 361-365.
Prasad et al., Lipase-catalysed regio-and enantioselective deacetylation of 2,4-diacetoxyphenyl alkyl ketones, Bioorganic & Medicinal Chemistry, vol. 7, 1999, pp. 1973-1977.
Bruttomesso et al., Lipase-catalysed deacetylation of androstane and pregnane derivatives: influence of ring D substitution, Journal of Molecular Catalysis B: Enzymatic, vol. 29, Jun. 21, 2004, pp. 149-153.
Adam, W. et al., Synthesis of optically active alpha-hydroxy acids by kinetic resolution through lipase-catalyzed enantioselective acetylation, European Journal of Organic Chemistry, (9), 1998, pp. 2013-2018.
Adam, W. et al., Lipase-catalyzed kinetic resolution of Z-configured homoallylic alcohols, Tetrahedron-Asymmetry, 10(2), 1999, 315-322.
Adam, W. et al., Preparation of optically active allylic hydroperoxy alcohols and 1,3-diols by enzyme-catalyzed kinetic resolution and photooxygenation of chiral homoallylic alcohols, Journal of Organic Chemistry, 65(5), 2000, pp. 1431-1433.
Akita, H., Recent advances in the use of immobilized lipases directed toward the asymmetric syntheses of complex molecules, Biocatalysis & Biotransformation, 13(3), 1996, pp. 141-156.
Akita, H., I. Umezawa, et al., Enzymatic hydrolysis in organic solvents for kinetic resolution of water-insoluble alpha-acyloxy esters with immobilized lipases, Chemical & Pharmaceutical Bulletin 45(2), 1997, pp. 272-278.
Ami, E. and H. Ohrui, Lipase-catalyzed kinetic resolution of (+/−)-trans-and cis-2-azidocycloalkanols, Bioscience Biotechnology & Biochemistry, 63(12), 1999, pp. 2150-2156.
Armesto, N., M. Ferrero, et al., Novel enzymatic synthesis of 4-O-cinnamoyl quinic and shikimic acid derivatives, Journal of Organic Chemistry, 68(14), 2003, pp. 5784-5787.
Kajiro, H., S. Mitamura, et al., Enantioselective synthesis of 2-hydroxy-1-indanone, a key precursor of enantiomerically pure 1-amino-2-indanol, Tetrahedron-Asymmetry, 9(6), 1998, pp. 907-910.
Allevi,P. et al, Lipase catalysed resolution of (R)-and (S)-1-trimethylsilyl-1-alkyn-3-ols: useful intermediates for the synthesis of optically active gamma-lactones, Tetrahedron: Asymmetry, vol. 8, No. 1, 1997, pp. 93-99.
Glanzer, B. et al., Enantioselective hydrolyses by baker's yeast-III microbial resolution of alkynyl esters using lyophilized yeast, Tetrahedron, vol. 43, No. 24, 1987, pp. 5791-5796.

*Primary Examiner*—Sandra Saucier
*Assistant Examiner*—Susan Hanley
(74) *Attorney, Agent, or Firm*—Pepper Hamilton LLP

(57) ABSTRACT

A process for preparing the compound of formula II by reacting the compound of formula I with an enzyme that can hydrolyze the ester bond:

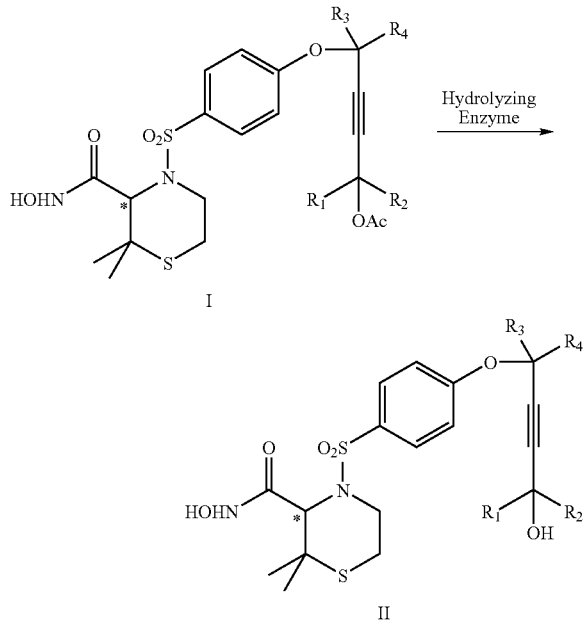

where * indicates a chiral center, $R_1$ and $R_2$ each independently represent H, $C_1$-$C_6$alkyl, —CN or —CCH, and $R_3$ and $R_4$ each independently represent H or $C_1$-$C_6$alkyl.

23 Claims, 1 Drawing Sheet

ENZYMATIC PROCESS FOR DEACETYLATION OF A PHENOXY-ALKYNYL ACETATE TO THE CORRESPONDING ALCOHOL

CROSS REFERENCE TO RELATED APPLICATIONS

This application claims priority benefit of U.S. Provisional Application Ser. No. 60/577,791 filed Jun. 8, 2004, which is incorporated by reference herein in its entirety.

FIELD OF THE INVENTION

This invention relates to processes for enzymatic hydrolysis of ester bonds to prepare target hydroxamic acids and derivatives and intermediates thereof.

BACKGROUND OF THE INVENTION

Chemical processes for hydrolysis of esters to alcohols are well-known. Typically, a base such as an alkali hydroxide or carbonate is used to cleave the ester linkage and produce the corresponding alcohol. These reactions require a highly alkaline pH, typically a pH of 11 or more, and relatively high temperatures, such as 45-50° C. or more.

A phenoxy-alkynyl acetate may be deacetylated with potassium carbonate at pH 11 and 45° C. However, the base hydrolysis reaction is fast and non-specific. If the reaction is not stopped in time, there is a risk that undesired impurities may form, leading to additional purification steps. Controlling the hydrolysis reaction creates a burden on the process control and personnel.

Enzymatic deacetylation can overcome many disadvantages of the base hydrolysis methods. Enzymatic processes are very specific, often providing a higher yield and purity than chemical processes. Additionally, enzymes usually function well near 37° C. and near neutral pH, so deacetylation may be performed at moderate temperatures and pH.

SUMMARY OF THE INVENTION

The present invention comprises a process for preparing the compound of formula II by reacting the compound of formula I with an enzyme that can hydrolyze the ester bond:

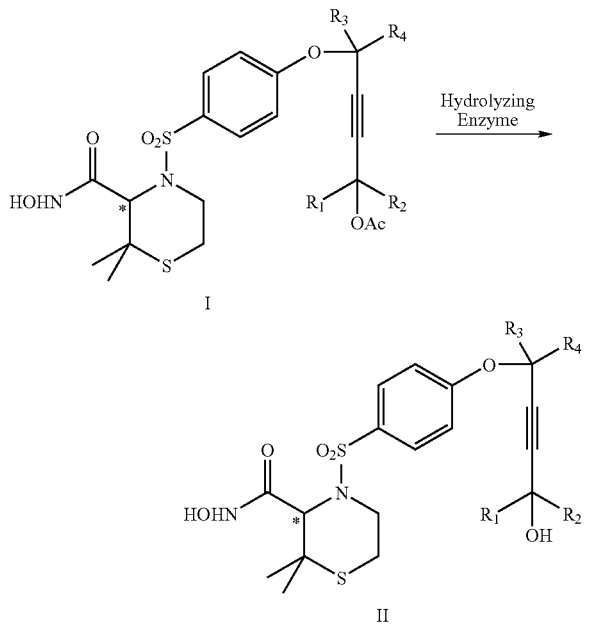

where * indicates a chiral center, $R_1$ and $R_2$ each independently represent H, $C_1$-$C_6$alkyl, —CN or —CCH, and $R_3$ and $R_4$ each independently represent H or $C_1$-$C_6$alkyl. Preferably, the enzyme is a lipase and the reaction occurs in an aqueous-organic co-solvent system. Suitable organic co-solvents are those that are soluble in water and in which the product alcohol will dissolve, including methanol, ethanol, propanol, isopropanol, THF, acetonitrile, diethoxyethane, and the like.

DETAILED DESCRIPTION

Figure 1:
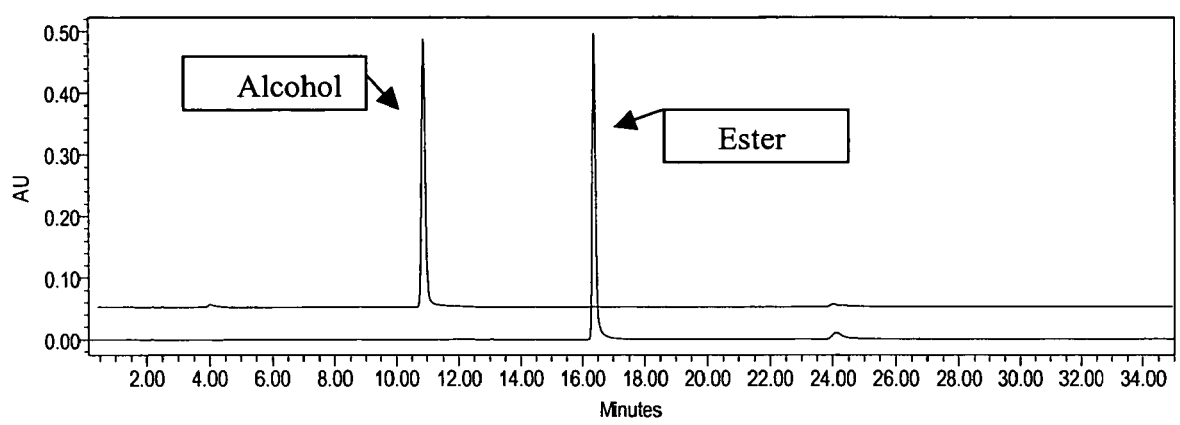
FIG. 1 illustrates the results of a High Performance Liquid Chromatography (HPLC) separation of 4-[4-({(3S)-3-[(hydroxyamino)carbonyl]-2,2-dimethyl-thiomorpholinyl}-sulfonyl)-phenoxy]-2-butynyl acetate and (3S)-N-hydroxy-4-({4-[(4-hydroxy-2-butynyl)oxy]phenyl}sulfonyl)-2,2-dimethyl-3-thiomorpholinecarboxamide.

The process of this invention includes reacting an enzyme, such as a lipase or esterase, with compound of formula I under conditions which enable the enzyme to be catalytically active. Suitable conditions are those in which the enzyme will be active and the product molecule will be stable. These conditions include a suitable pH (above about 5.5), a suitable temperature, and a suitable reaction medium.

The enzymatic hydrolysis reaction overcomes many of the disadvantages of the typical base hydrolysis reaction by offering robust reaction conditions and specific chemical bond cleavage under mild reaction conditions and at a substrate concentration ranging from 1 to 200 g/L in an organic solvent-aqueous buffer mixture. The enzymatic hydrolysis may take up to 68 hours or more, depending on the reaction conditions employed, but can be carried out in less than 24 hours under suitable conditions. This process is capable of providing total conversion of the starting material to the desired product. In addition, the process offers about two to three times greater volumetric reactor productivity compared to the chemical process, saving personnel time and organic solvents.

After the enzymatic reaction is complete, the alcohol of formula II will be in solution due to the co-solvent. This alcohol is not soluble in water, however, and may be precipitated by adding more water to the reaction mixture and lowering the temperature, preferably to below about 10° C., for example about 0-10° C., and most preferably to about 4° C. The precipitate then may conveniently be collected by filtration and washed with additional water to eliminate water-soluble impurities. Optionally, it may be recrystallized for further purification, for example by dissolving it in a mixture of water and co-solvent at room temperature and repeating the process of precipitation.

During enzymatic ester hydrolysis, the pH of the reaction should be maintained so that the acid released does not lower the pH enough to stop the enzyme activity. The reaction conditions employed must keep the pH within the range in which the enzyme remains catalytically active. For maintaining the pH of the reaction, any suitable buffer known in the art can be used, such as, for example, potassium phosphate, 4-morpholineethanesulfonic acid monohydrate (MES), bis(2-hydroxyethyl)amino-tris(hydroxymethyl)methane (Bis-Tris), tris(hydroxymethyl) amino methane hydrochloride (Tris-HCl), 3-(N-morpholino)-propanesulfonic acid (MOPS), 3-(N-morpholino)-2-hydroxypropanesulfonic acid (MOPSO), N,N-bis(2-hydroxyethyl)-2-aminoethanesulfonic acid (BES), N-tris(hydroxymethyl)methyl-2-aminoethane sulfonic acid (TES), 4-(2-hydroxyethyl)-1-piperazineethanesulfonic acid (HEPES) and the like. Alternatively, the reaction pH can be controlled by addition of a suitable base using a pH-stat, intermittent addition of dibasic buffer salt, or by any other means to maintain the pH within the range at which the enzyme remains active. A pH above 5.5 and below about 8.0 is desirable in the process of this invention. Preferably the pH is maintained between 6.0 and 7.0.

The temperature should be maintained in a range in which the enzyme maintains its catalytic activity, which is typically between room temperature (about 20-25° C.) and about 60° C. Preferably the reaction will be carried out at or near 37° C., such as in the approximate range of 26-42° C. Although the enzyme may be active up to about 60° C., such a high temperature may cause some degradation of the product. For this reason, the temperature should not exceed about 45° C., and preferably should not exceed about 42° C. A temperature in the approximate range of 30-40° C. is recommended for this process, because the enzyme will be sufficiently active to produce a high yield in a reasonably short time period and the product will not be significantly degraded, resulting in greater yield and purity of the product.

Any suitable hydrolyzing enzyme known in the art may be used in the practice of this invention, such as lipase and esterase enzymes. Lipase enzymes are preferred in the practice of this invention, for example, *Candida antarctica* Lipase type B, and the like. The enzyme may be in liquid form or immobilized on an inert support, such as a bead, by adsorption or covalent bonding.

In a preferred embodiment of this invention, the enzyme is immobilized on an inert support structure in the form of beads. After the deacylation of the compound of formula I exceeds 99% completion, the reaction medium is filtered to remove the enzyme beads. Then the reaction medium is reduced in volume to about half in vacuo and cold water is added to initiate crystallization of the product compound. The reaction medium preferably is stirred under cold conditions for an additional 4-6 h and then the crystallized product is collected by filtration, washing, and drying in vacuo at about 45° C.

The enzyme used in this invention may also be used in liquid form, i.e., dissolved, suspended, or otherwise dispersed in a liquid medium suitable for use in the practice of this invention.

Preferably, the liquid medium is a mixture of water and a water-soluble organic co-solvent that will dissolve the product alcohol, will not interfere with the reaction, and in which the enzyme will be active. Suitable organic co-solvents include alcohols, such as $C_1$-$C_6$ straight, branched or cyclic alcohols, (e.g., methanol, ethanol, propanol and isopropanol), and other polar solvents, such as tetrahydofuran (THF), diethoxyethane, and acetonitrile. Those skilled in the art will readily be able to identify suitable co-solvents without undue experimentation.

The organic co-solvent must be present in sufficient concentration to dissolve the product alcohol, typically at least about 40% by weight, and more preferably at least about 50%. Sufficient water is needed to dissolve the buffer and facilitate the reaction between the enzyme and the reactant. Typically, at least about 25% water, more preferably at least about 30% water, is used. Preferred solvent mixtures in the practice of this invention contain approximately 40% to 70% organic co-solvent and approximately 30 to 60% water by weight.

In one embodiment of the present invention, $R_{1-4}$ are all H, and the compounds of formulae I and II are (S)-isomers. However, the applicability of the process of this invention is not limited to (S)-isomers, nor to compounds in which $R_{1-4}$ are all H.

A particularly preferred embodiment of this invention is a process for deacetylation of 4-[4-({(3S)-3-[(hydroxyamino) carbonyl]-2,2-dimethyl-thiomorpholinyl}-sulfonyl)-phenoxy]-2-butynyl acetate to the corresponding alcohol, (3S)-N-hydroxy-4-({4-[(4-hydroxy-2-butynyl)oxy] phenyl}sulfonyl)-2,2-dimethyl-3-thiomorpholinecarboxamide, a compound useful for treating, for example, arthritis and inflammation. This process can be carried out with a commercially available lipase under mild reaction conditions in the presence of a co-solvent in a buffered solution. The product compound is recovered from the enzyme reaction by filtration to remove the enzyme support beads, reduction of the reaction volume in vacuo, and then crystallization of the product from the water-enriched solution.

A compound of formula I may be made by any suitable process, for example, by reacting a compound of formula III with a silyl ester of (3S)-2,2-dimethyl-tetrahydro-2H-1,4-thiazine-3-carboxylic acid:

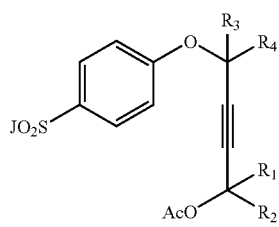

III wherein J represents chlorine, bromine, fluorine, 1,2,4-triazolyl, benzotriazolyl or imidazolyl.

One method for making the compound of formula III is to react a compound of formula IV with a halogenating agent such as thionyl chloride, oxalyl chloride, phosphorus pentachloride, phosphorus oxychloride, thionyl bromide, and the like. The halide may be converted to another J group listed above by reaction with an appropriate compound, such as 1,2,4-triazole, benzotriazole or imidazole. One method for making the compound of formula IV comprises alkylating a compound of formula V, or a salt or solvate thereof, with a compound of formula VI to form the compound of formula IV

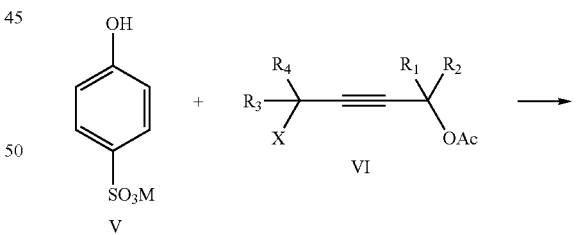

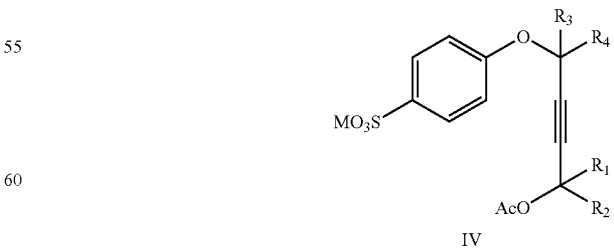

IV wherein M is hydrogen, lithium, sodium, potassium, cesium, magnesium, copper or zinc and X is a suitable leaving group, such as halogen, mesylate or tosylate.

The following examples are presented to illustrate certain embodiments of the present invention, but should not be construed as limiting the scope of this invention.

HPLC method: Column: C18-Symmetry (Waters Corp.) 4 mm×75 mM. Solvent A: 10% acetonitrile in 10 mM ammonium acetate. Solvent B: 80% acetonitrile in 10 mM ammonium acetate. Gradient: 90% A, 10% B at zero time to 60% B in 10 min.; 100% B from 11 min. to 15 min.; continue 100% B to 20 min. Detection by UV at 254 nm. Alternatively, any other suitable HPLC column capable of separating the ester from product alcohol could be used. In all the following examples the reaction was monitored by HPLC analysis. FIG. 1 shows the results of an HPLC separation of the ester and alcohol of Example 1 using this method.

EXAMPLE 1

Reaction with Enzyme in Ethyl Alcohol-Aqueous Buffer Mixture

A glass vessel was charged with 1 g 4-[4-({(3S)-3-[(hydroxyamino)-carbonyl]-2,2-dimethyl-thiomorpholinyl}-sulfonyl)-phenoxy]-2-butynyl acetate in 50% aqueous ethanol-150 mM potassium phosphate buffer at pH 6.5. To this, Candida antarctica Lipase type B immobilized on a synthetic support (NOVOZYM 435, Novozymes North America, Franklinton, N.C.) was added at 10 g/L. The total reaction volume was 10 ml and the incubation temperature was 37° C. The reaction was monitored by sampling and analysis by HPLC. By 68 h all the substrate was converted to the deacylated product, (3S)-N-hydroxy-4-({4-[(4-hydroxy-2-butynyl)oxy] phenyl}sulfonyl)-2,2-dimethyl-3-thiomorpholinecarboxamide. The immobilized enzyme beads were separated by filtration and 10 mL of water was added. The reaction mixture was cooled to 4° C. and the mixture was left overnight to crystallize the compound. The product crystals were recovered by filtration and washed with distilled water to remove any buffer salts. The purity of the product was determined to be 98% by HPLC, and the strength was about 93.9. The starting material impurity was about 0.2%.

EXAMPLE 2

Different Organic Solvents for Lipase Hydrolysis Reaction Medium

Methanol, ethanol, isopropanol and tetrahydrofuran at 50% concentration in aqueous potassium phosphate buffered reaction mixtures containing 7.5 g/L immobilized enzyme (NOVOZYM 435, Novozymes North America, Franklinton, N.C.) and 100 g/L 4-[4-({(3S)-3-[(hydroxyamino)carbonyl]-2,2-dimethyl-thiomorpholinyl}-sulfonyl)-phenoxy]-2-butynyl acetate were tested separately. The reaction temperature was 37° C. in each case. By 24 h, the deacylation reaction progressed to about 99% completion in the ethyl alcohol, isopropanol and THF reaction mixtures, while in the methanol-buffer system, the reaction reached about 60% completion.

EXAMPLE 3

Effect of Buffer PH and Enzyme Concentration on Deacylation of 4-[4-({(3S)-3-[(HYDROXYAMINO) CARBONYL]-2,2-DIMETHYL-THIOMORPHOLINYL}-SULFONYL)-PHENOXY]-2-BUTYNYL ACETATE A set of reactions was performed with 75 mM potassium phosphate buffer having pH 5.5, 6.0, and 6.5 and enzyme concentrations of 2, 5 and 10 g/L (NOVOZYM 435, Novozymes North America, Franklinton, N.C.). The substrate concentration and ethanol concentration were fixed at 100 g/L and 50%, respectively, and the reaction temperature was 37° C. After 24 h, the reactions at pH 5.5 were less than 90% complete. In the reactions where enzyme concentration was 2 g/L, the conversion was also less than 90%, even when the pH was 6.5. The results indicate that for efficient conversion of the substrate, the enzyme reaction pH preferably should be above 5.5 and the immobilized enzyme concentration above 2 g/L.

EXAMPLE 4

Testing Soluble Form of Lipase for Deacylation Reaction of 4-[4-({(3S)-3-[(HYDROXYAMINO) CARBONYL]-2,2-DIMETHYL-THIOMORPHOLINYL}-SULFONYL)-PHENOXY]-2-BUTYNYL ACETATE C. antarctica lipase B in liquid form (BioCatalytics Inc., Pasadena, Calif.) was used for the deacylation of 4-[4-({(3S)-3-[(hydroxyamino)carbonyl]-2,2-dimethyl-thiomorpholinyl}-sulfonyl)-phenoxy]-2-butynyl acetate. Reactions were performed using 10 mL/L lipase and 150 g/L of the ester substrate in 50 and 60% ethyl alcohol/water with a pH 6.5 potassium phosphate buffer. The substrate deacylation reaction reached more than 99% completion within 24 h at both ethanol concentrations.

EXAMPLE 5

Enzymatic Deacylation of 4-[4-({(3S)-3-[(HYDROXYAMINO)CARBONYL]-2,2-DIMETHYL-THIOMORPHOLINYL}-SULFONYL)-PHENOXY]-2-BUTYNYL ACETATE at Large Scale in Isopropanol-Aqueous Buffer A jacketed glass reactor equilibrated to 37° C. was charged with 99 g 4-[4-({(3S)-3-[(hydroxyamino)carbonyl]-2,2-dimethyl-thiomorpholinyl}-sulfonyl)-phenoxy]-2-butynyl acetate and 400 mL isopropanol, and the contents were mixed with an overhead stirrer. To this vessel, 260 mL potassium phosphate buffer (pH 6.6) was added with continued mixing. About 5.5 g of immobilized Candida antarctica Lipase B (NOVOZYM 435, Novozymes North America, Franklinton, N.C.) was added with continued mixing. By 24 h, the starting material conversion was about 98.5%. The reaction mixture was filtered to remove the immobilized enzyme beads and evaporated in vacuo to remove isopropanol and reduce the volume to about half the original volume. Cold water was added to the reaction mixture while cooling to about 4° C. The product crystallized out as the water content increased. The crystals were collected by filtration and the buffer salts were removed by washing the product crystals with several volumes of cold distilled water. The product was dried in vacuo at 45° C. to yield about 82.25 g (92% yield). Optionally the product can be recrystallized from an isopropanol-water mixture to improve the purity.

Many variations of the present invention not illustrated herein will occur to those skilled in the art. The present invention is not limited to the embodiments illustrated and described herein, but encompasses all the subject matter within the scope of the appended claims.

What is claimed is:

1. A process for preparing a compound of formula II:

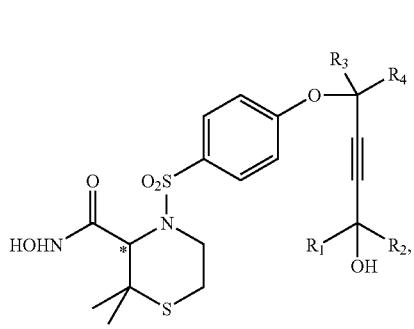

said process comprising reacting a compound of formula I:

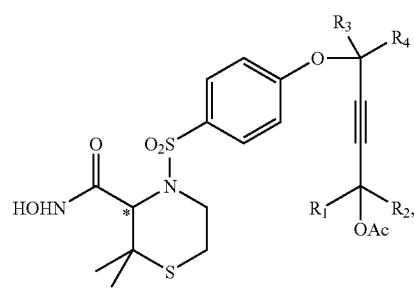

in a suitable solvent and at a suitable temperature and pH, with an ester hydrolyzing enzyme, wherein:

* indicates a chiral center, $R_1$ and $R_2$ are each independently selected from the group consisting of H, $C_1$-$C_6$alkyl, —CN and —CCH, and $R_3$ and $R_4$ are each independently selected from the group consisting of H and $C_1$-$C_6$alkyl.

2. The process of claim 1 wherein the solvent comprises a mixture of water and an organic co-solvent, the temperature is in the range of about 26-42° C., and the pH is in the range of about 6.0-8.0.

3. The process of claim 2 wherein the organic co-solvent is selected from the group consisting of $C_1$-$C_6$ straight, branched or cyclic alcohols, tetrahydrofuran, acetonitrile, and diethoxyethane.

4. The process of claim 2 wherein the mixture of water and organic co-solvent comprises about 30-60% water by weight.

5. The process of claim 1 wherein the enzyme is a lipase.

6. The process of claim 5 wherein the lipase is *Candida antarctica* Lipase type B.

7. The process of claim 5 wherein the lipase is immobilized on an inert support structure.

8. The process of claim 1 wherein $R_1$, $R_2$, $R_3$ and $R_4$ are all H.

9. The process of claim 8 wherein the compounds of formulae I and II are (S)-isomers at the * chiral center.

10. The process of claim 1 further comprising precipitating the compound of formula II by adding water to the reaction mixture.

11. A process for preparing the compound of formula II:

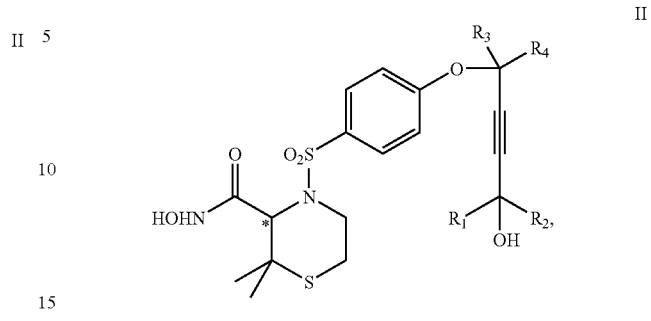

wherein * indicates a chiral center, $R_1$ and $R_2$ are each independently selected from the group consisting of H, $C_1$-$C_6$alkyl, —CN and —CCH, and $R_3$ and $R_4$ are each independently selected from the group consisting of H and $C_1$-$C_6$alkyl, said process comprising the steps of:

a) forming a reaction mixture comprising the compound of formula I:

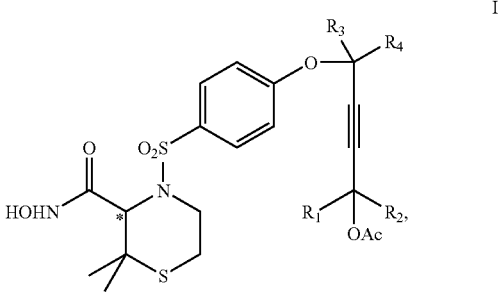

an ester hydrolyzing enzyme, a mixture of water and an organic co-solvent, and a buffering agent which functions to maintain the pH in the range of about 6.0-8.0; and b) maintaining the reaction mixture at a temperature in the range of about 26-42° C. for a time sufficient to allow the enzyme to convert the compound of formula I to the compound of formula II.

12. The process of claim 11 further comprising the step of:

c) reducing the temperature to below about 10° C. and adding water to cause precipitation of the compound of formula II.

13. The process of claim 11 wherein the mixture of water and organic co-solvent is about 30-60% water by weight and the organic co-solvent is selected from the group consisting of $C_1$-$C_6$ straight, branched or cyclic alcohols, tetrahydrofuran, acetonitrile, and diethoxyethane.

14. The method of claim 11 wherein the enzyme is a lipase and the buffering agent functions to maintain the pH in the range of about 6.0-7.0.

15. The process of claim 14 wherein the lipase is *Candida antarctica* Lipase type B.

16. The process of claim 14 wherein the lipase is immobilized on an inert support structure.

17. A process for preparing a compound of formula II-a:

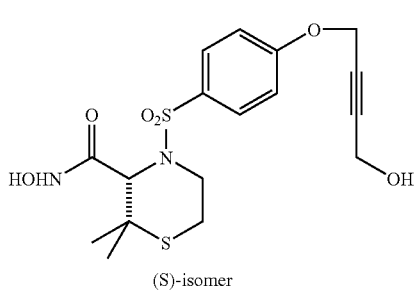

(S)-isomer said process comprising the steps of:
a) forming a reaction mixture comprising a compound of formula I-a:

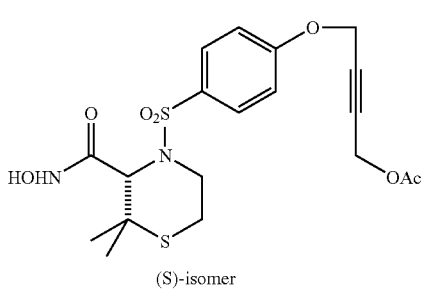

(S)-isomer a lipase, a mixture of water and an organic co-solvent which is about 30-60% water by weight, and a buffering agent which functions to maintain the pH in the range of about 6.0-8.0; and b) maintaining the reaction mixture at a temperature in the range of about 26-42° C. for a time sufficient to allow the enzyme to convert the compound of formula I-a to the compound of formula II-a.

18. The process of claim 17 wherein the co-solvent is selected from the group consisting of $C_1$-$C_6$ straight, branched or cyclic alcohols, tetrahydrofuran, acetonitrile, and diethoxyethane.

19. The process of claim 18 wherein the co-solvent is selected from the group consisting of methanol, ethanol, propanol, isopropanol, tetrahydrofuran, acetonitrile, and diethoxyethane.

20. The process of claim 17 wherein the buffering agent comprises potassium phosphate and the pH of the reaction mixture is maintained in the range of about 6.0-7.0.

21. The process of claim 17 wherein the lipase is *Candida antarctica* Lipase type B, and in step b) the temperature is in the range of about 30-40° C.

22. The process of claim 17 further comprising the step of:
c) reducing the temperature to about 0-10° C. and adding water to cause precipitation of the compound of formula II-a.

23. The process of claim 17 wherein the lipase is immobilized on an inert support structure.

* * * * *